United States Patent
Schiffman

(10) Patent No.: US 8,207,129 B2
(45) Date of Patent: *Jun. 26, 2012

(54) TREATMENT WITH CYCLOSPORIN A

(75) Inventor: Rhett M. Schiffman, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 247 days.

This patent is subject to a terminal disclaimer.

(21) Appl. No.: 12/497,886

(22) Filed: Jul. 6, 2009

(65) Prior Publication Data

US 2009/0264348 A1    Oct. 22, 2009

Related U.S. Application Data

(63) Continuation of application No. 11/681,152, filed on Mar. 1, 2007, now Pat. No. 7,557,082.

(60) Provisional application No. 60/779,120, filed on Mar. 3, 2006.

(51) Int. Cl.
*A61K 38/00* (2006.01)
*A61K 38/12* (2006.01)
*A61K 38/13* (2006.01)

(52) U.S. Cl. ............................... 514/20.5; 514/20.8

(58) Field of Classification Search .................. None
See application file for complete search history.

(56) References Cited

FOREIGN PATENT DOCUMENTS

| GB | 2224205 | 5/1990 |
|---|---|---|
| WO | WO89/01772 | 3/1989 |
| WO | WO03/030834 | 10/2002 |

OTHER PUBLICATIONS

Cerulli L and Missiroli F, Chapter 4, "Agining of the Cornea", Agin Medicine: Age-Related Changes of the Human Eye, C.A.P. Cavallotti and L. Cerulli, Human Presse, Totowa, NJ. 2008.
Vision Loss from Centers for Disease Control "NPL-CDC-vision_loss.pdf", Accessed Apr. 2, 2008.
Akpek RK, Dart JK, Watson S, Christen W, Dursun D, Yoo S, O'Brien TP, Schein OD, Gottsch JD, A Randomized Trial of Topical Cyclosporin 0.05% in Topical Steroid-Resistant Atopic Keratoconjunctivitis, Ophthalmology, 2004, 111:476-482.
Acute Vision Loss from the Merck Manual NPL-Merck manual-acute vision loss.pdf, Accessed Apr. 2, 2008.
Eye Symptoms-Symptoms from the Merck Manual NPL-Merck manual-eye symptoms-symptoms.pdf, Accessed Apr. 2, 2008.
Vision Loss from NIH—"NPL-NIH-vision lo9ss.pdf", Accessed Apr. 2, 2008.

*Primary Examiner* — Julie Ha
(74) *Attorney, Agent, or Firm* — Joel B. German; Debra D. Condino; Allergan, Inc.

(57) ABSTRACT

Disclosed herein is a method comprising administering cyclosporin A topically to an eye of a person for the purpose of treating or preventing loss of vision from keratoconus.

6 Claims, No Drawings

TREATMENT WITH CYCLOSPORIN A

CROSS-REFERENCE TO RELATED APPLICATION

This application is a continuation of U.S. patent application Ser. No. 11/681,152, filed on Mar. 1, 2007, now U.S. Pat. No. 7,557,082, which claims priority under 35 U.S.C. §120 to U.S. Provisional Patent Application No. 60/779,120 filed on Mar. 3, 2006, and which is incorporated herein by reference.

DESCRIPTION

Keratoconus is a bilateral ocular disorder that progressively thins and distorts the central portion of the cornea toward a conic shape, typically leading to substantial visual impairment and corneal scarring. Distortion of the cornea in keratoconus results from decreased resilience and low mechanical strength of the corneal tissues (Wollensak et al., Fortschr. Ophthalmol. 84:28-32, 1987, incorporated herein by reference). These structural defects represent important pathogenetic factors in the disease (Edmund, Acta Ophthalmol. 66:134-140, 1988, incorporated herein by reference), however the mechanisms that cause these structural changes remain undefined.

To date, no specific tools have been developed to treat or prevent keratoconus. In the mildest cases, management involves the use of spectacles or soft contact lenses. More commonly, early stage management of keratoconus requires specially designed contact lenses that compensate visual defects and provide some structural support to correct corneal distortion. More advanced presentations are managed with rigid gas-permeable (RGP) contact lenses to minimize corneal distortion and correct irregular astigmatism (Koliopoulos et al., Ann. Ophthalmol. 13(7):835-7, 1981, incorporated herein by reference). If satisfactory wearing time is not achieved with contact lens, or if the contact lens-corrected vision is not adequate (which may result from corneal scarring or poor fitting of the steeply sloped cone) keratoplasty is indicated.

Even with the aid of the foregoing management tools, the vision of patients with keratoconus often deteriorates beyond correction. At this point the replacement of corneal tissue by transplantation becomes the indicated treatment option. Corneal transplantation is necessary for 10% to 20% of patients with keratoconus (Kennedy et al., Am. J. Ophthalmol. 101 (3):267-73, 1986; and Smiddy et al., Ophthalmol 95:487-92, 1988, each incorporated herein by reference). However, corneal transplantation is attended by high costs, limitation of the supply of suitable corneas, and substantial risks, including risks of adverse sequelae from anesthesia, transplant failure, and transmission of tissue-borne pathogens (e.g., HIV virus) from donor tissue to the transplant recipient.

In addition to visual defects, the medical history of keratoconus patients often elicits allergic or systemic conditions. Atopic disease (allergy) is present in approximately 35% of cases (Rahi et al., Br. J. Ophthalmol. 61:761-4, 1977, incorporated herein by reference). Eye rubbing, possibly a response to allergic discomfort, is reported by 20% of patients with keratoconus (Ridley, Br. J. Ophthalmol. 45:631, 1961, incorporated herein by reference). In addition, keratoconus has been associated with inherited systemic diseases such as Down syndrome, Lebers congenital amaurosis, osteogenesis imperfecta, and connective tissue disorders such as Ehler-Danlos syndrome.

Disclosed herein is a method of treating or preventing loss of vision from thinning of the cornea.

In one embodiment, said thinning of the cornea causes distortion of the shape of the cornea.

In another embodiment, said distortion of the shape of the cornea is keratoconus.

In another embodiment, said distortion of the shape of the cornea is keratoglobus.

In another embodiment, said distortion of the shape of the cornea is Pellucid marginal degeneration.

These methods comprises topically administering cyclosporin A to the eye of a person for the treatment of keratoconus. While not intending to limit the scope of the invention in any way, the cyclosporin A may be administered topically in a solution or an emulsion.

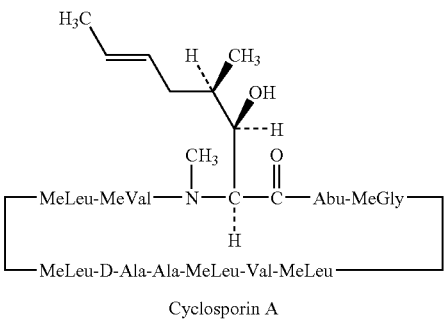

Cyclosporin A

Cyclosporin A is a cyclic peptide with immunosuppressive properties having the structure shown above. It is also known by other names including cyclosporine, cyclosporine A, ciclosporin, and ciclosporin A.

For a topical liquid comprising cyclosporin A, the concentration of cyclosporin A may be readily determined by a person of ordinary skill in the art. Generally, this is from about 0.005 to about 5% by weight, although higher or lower concentrations may also be useful. In one embodiment, the concentration of cyclosporin A is from about 0.02% to about 0.15% by weight.

Useful compositions are disclosed in the following patent applications, each of which is expressly incorporated by reference herein: U.S. patent application Ser. No. 11/181,409, filed on Jul. 13, 2005; U.S. patent application Ser. No. 11/181,509, filed on Jul. 13, 2005; U.S. patent application Ser. No. 11/181,187, filed on Jul. 13, 2005; U.S. patent application Ser. No. 11/181,178, filed on Jul. 13, 2005; U.S. patent application Ser. No. 11/181,428, filed on Jul. 13, 2005; U.S. patent application Ser. No. 11/255,821, filed on Oct. 19, 2005; U.S. patent application Ser. No. 11/161,218, filed on Jul. 27, 2005; and U.S. Provisional Patent Application Ser. No. 60/727,684, filed on Oct. 17, 2005.

In one embodiment, the cyclosporin A is administered in the form of Restasis®, available from Allergan, Inc. The cyclosporin A is administered twice a day as indicated on the package insert.

Compositions disclosed in U.S. Provisional Patent Application 60/829,808, Filed Oct. 17, 2006, are particularly useful formulations of cyclosporin A.

EXAMPLE 1

A patient suffering from visual impairment due to keratoconus is administered 0.05% cyclosporin A, in the form of Restasis®, twice a day. After six months, substantial improvement in the patient's vision is observed. Treatment continues for another six months.

Although there has been hereinabove described pharmaceutical compositions for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the present invention as defined in the appended claims.

What is claimed is:

1. A method of treating impaired vision due to keratoconus, the method comprising topically administering to an eye of person having such impaired vision a composition comprising cyclosporin A.

2. The method of claim 1, wherein the composition comprises about 0.005% to about 0.15% cyclosporin A by weight.

3. The method of claim 1, wherein the composition comprises 0.005% to 0.15% cyclosporin A by weight.

4. The method of claim 3, wherein the composition comprises 0.005% cyclosporin A by weight.

5. The method of claim 3, wherein the composition comprises 0.02% cyclosporin A by weight.

6. The method of claim 3, wherein the composition comprises 0.05% cyclosporin A by weight.

\* \* \* \* \*

UNITED STATES PATENT AND TRADEMARK OFFICE
CERTIFICATE OF CORRECTION

| | | |
|---|---|---|
| PATENT NO. | : 8,207,129 B2 | Page 1 of 1 |
| APPLICATION NO. | : 12/497886 | |
| DATED | : June 26, 2012 | |
| INVENTOR(S) | : Rhett M. Schiffman | |

It is certified that error appears in the above-identified patent and that said Letters Patent is hereby corrected as shown below:

On the Title page, in field (56), under "Other Publications", in column 2, line 1, delete ""Agining" and insert -- "Aging --, therefor.

On the Title page, in field (56), under "Other Publications", in column 2, line 14, delete "lo9ss.pdf'," and insert -- loss.pdf', --, therefor.

In column 1, line 47, delete "Ophthalmol" and insert -- Ophthalmology --, therefor.

Signed and Sealed this
Fourth Day of September, 2012

David J. Kappos
*Director of the United States Patent and Trademark Office*